(12) United States Patent
Frasca

(10) Patent No.: US 7,249,521 B1
(45) Date of Patent: Jul. 31, 2007

(54) METHOD FOR DETERMINING THE PRESENCE OF A MAGNETICALLY SUSCEPTIBLE OR MAGNETIC MATERIAL IN A SAMPLE

(76) Inventor: Peter Frasca, 107 Haddon Ave., Westmont, NJ (US) 08108

( * ) Notice: Subject to any disclaimer, the term of this patent is extended or adjusted under 35 U.S.C. 154(b) by 0 days.

(21) Appl. No.: 11/211,774

(22) Filed: Aug. 24, 2005

(51) Int. Cl.
*G01N 19/08* (2006.01)
*G01N 29/04* (2006.01)

(52) U.S. Cl. ........................................ 73/799
(58) Field of Classification Search ............ 73/799
See application file for complete search history.

(56) References Cited

U.S. PATENT DOCUMENTS

| | | | |
|---|---|---|---|
| 3,620,316 A | | 11/1971 | Henry et al. |
| 6,100,687 A | * | 8/2000 | Weitekamp et al. ........ 324/300 |
| 6,605,941 B2 | * | 8/2003 | Abe ............................ 324/244 |
| 2003/0224366 A1 | | 12/2003 | Weindel et al. |

FOREIGN PATENT DOCUMENTS

JP  11183238  7/1999

* cited by examiner

Primary Examiner—Michael Cygan
Assistant Examiner—O. Davis
(74) Attorney, Agent, or Firm—Norman E. Lehrer

(57) ABSTRACT

The present invention is based on the recognition that some materials contain a magnetically susceptible or magnetic component. That is, they exhibit ferromagnetic, paramagnetic, diamagnetic or magnetic properties. According to the invention, it is possible to determine the presence of a magnetically susceptible or magnetic component in a sample of a material by obtaining a sample of the material, positioning the sample at a predetermined distance from a magnet and then measuring the magnetic force on the sample by the magnet. The force is measured using a force transducer. To obtain the magnetic force per unit gravitational force, the gravitational force on the sample is measured out of the presence of the magnet and the measured magnetic force is then divided by the gravitational force exerted on the sample. A sample thickness adjustment is necessary if comparing samples of different thicknesses.

4 Claims, 1 Drawing Sheet

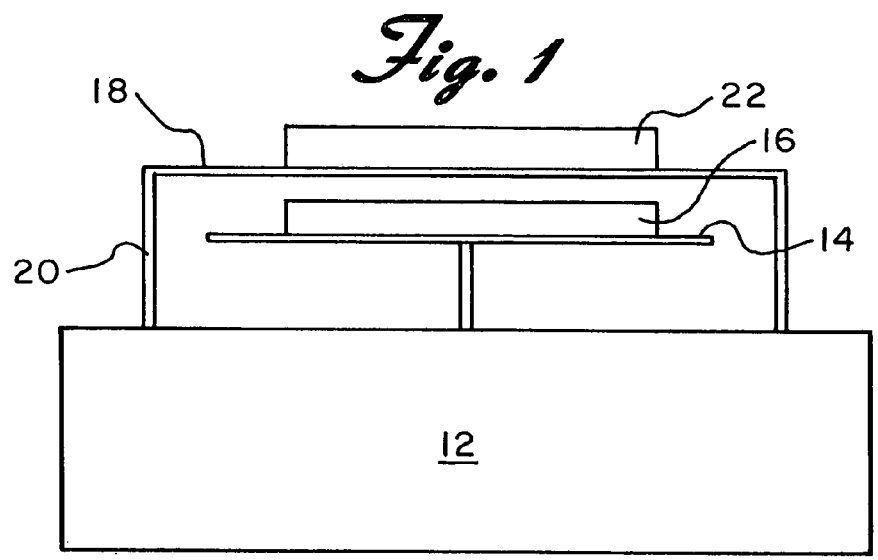
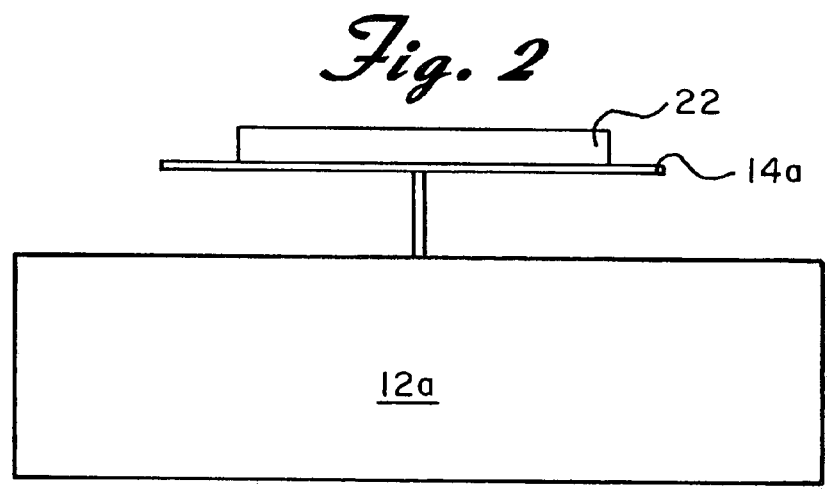
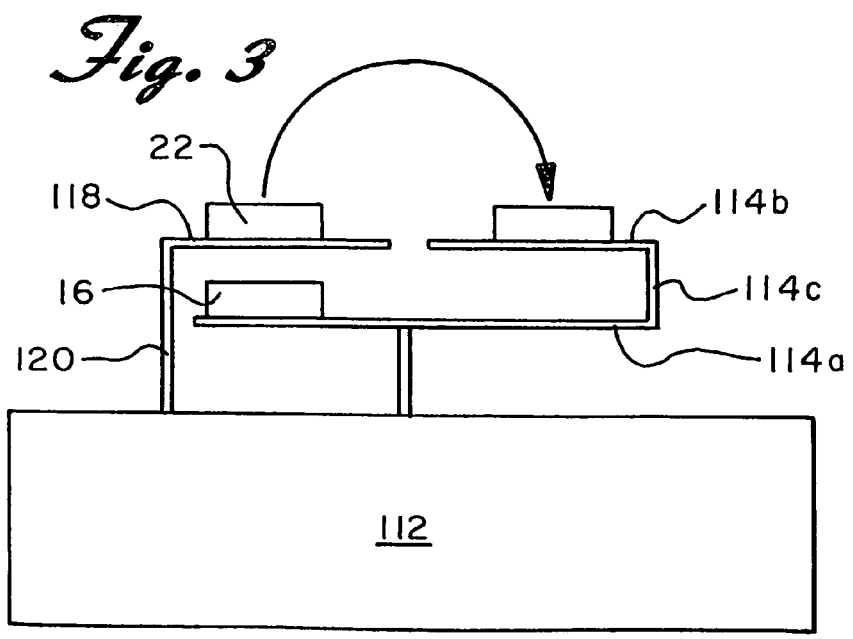

METHOD FOR DETERMINING THE PRESENCE OF A MAGNETICALLY SUSCEPTIBLE OR MAGNETIC MATERIAL IN A SAMPLE

BACKGROUND OF THE INVENTION

The present invention is directed toward a method for determining the presence of a magnetically susceptible or magnetic substance in a sample of a material and, more particularly, toward a method for determining the presence of asbestos in a sample material.

Although previously widely used as in insulation and in various other building materials, it is now known that asbestos, particularly in dust form, can cause various serious diseases such as lung cancer. While asbestos is no longer used, older buildings may contain significant quantities of asbestos in various materials from which the building may have been constructed. This normally does not create a problem as long as the structure is not disturbed since it is primarily asbestos dust that is known to be carcinogenic.

The problem manifests itself primarily when a building is being renovated. And such renovations need not be major. For example, a building owner or contractor may be replacing or removing floor tiles.

When ceiling and/or floor tiles or the like are being removed, they frequently must be broken up into pieces which can create substantial dust. This is exacerbated by the fact that such renovations are normally done in a closed space whereby the dust would be breathed in by the workers.

While many older ceiling or floor tiles and other building materials contained asbestos, not all of them did. If the tiles or other building materials being ripped up do not contain asbestos, then the dust that may be produced can easily be controlled by the use of ventilation fans or the like. Under such circumstances, the dust simply becomes a nuisance. If, however, the building materials and, therefore, the dust contains asbestos, OSHA and other health laws require that the asbestos be removed utilizing very specific procedures. These include, inter alia, totally sealing the room or building being renovated and utilizing specified ventilation with appropriate filtering equipment. Such procedures can greatly add to the cost of a project.

SUMMARY OF THE INVENTION

It is an object of the present invention to provide a method for quickly and inexpensively screening a sample of a material to determine the presence of a magnetically susceptible or magnetic component such as asbestos within a sample of a material.

This object can be achieved by the present invention based on the recognition that some materials contain constituents that are magnetically susceptible or magnetic. That is, they exhibit ferromagnetic, paramagnetic or diamagnetic properties. According to the invention, it is possible to determine the presence of magnetically susceptible or magnetic components in a sample of a material by obtaining a sample of the material, positioning the sample at a predetermined distance from a magnet and then measuring the magnetic force on the sample by the magnet. The force is measured using a system consisting of a force transducer and associated electronics. To obtain the magnetic force (exerted on the sample) per unit gravitational force exerted on the sample, the gravitational force on the sample is measured out of the presence of the magnet and the measured magnetic force on the sample is then divided by the gravitational force exerted on the sample.

Other objects, features and advantages of the invention will be readily apparent from the following detailed description of preferred embodiments thereof taken in conjunction with the drawings.

BRIEF DESCRIPTION OF THE DRAWINGS

For the purpose of illustrating the invention, there is shown in the accompanying drawings forms, which are presently, preferred; it being understood that the invention is not intended to be limited to the precise arrangements and instrumentalities shown.

FIG. 1 is a schematic representation illustrating the principles of the present invention;

FIG. 2 is a schematic representation of a standard force transducer useful with the device shown in FIG. 1, and FIG. 3 is a schematic representation of a modified form of the procedure demonstrated in FIGS. 1 and 2.

DETAILED DESCRIPTION OF THE PREFERRED EMBODIMENT

Referring now to the drawings in detail wherein like reference numerals have been used in the two figures to designate like elements, there is shown in FIG. 1 a schematic representation of an arrangement useful for practicing the method of the present invention.

More particularly, FIG. 1 shows a device comprised of a force transducer 12 with associated electronics. Placed and secured on the platform 14 of the force transducer 12 is a permanent magnet 16. Located at a fixed distance above the magnet 16 is a support platform 18. The platform 18 is supported by legs 20 that may rest on the body of the force transducer assembly 12 but are not in contact with the force transducer platform 14.

After zeroing out the force transducer to remove the gravitational force exerted on the magnet 16, the sample 22 to be analyzed is placed on the fixed platform 18 above the magnet 16 in a position so as to cover as much as possible the area above the magnet. The magnetic force on the sample 22 is determined by the force exerted by the sample 22 on the magnet 16 (or vice versa).

The magnetic force (F) on the sample is normalized by dividing the magnetic force F by the gravitational force (G) exerted on the sample (as measured by the conventional force transducer 12a shown in FIG. 2) to obtain F/G.

Alternatively, a simple modification to the force transducer device shown in FIG. 1 can be made so that the same device can be used to measure both the magnetic force and the gravitational force on the sample 22. Such an arrangement is shown, for example, in FIG. 3.

The force transducer system 112 shown in FIG. 3 can be essentially the same as the force transducer system 12 of FIG. 1. However, the platform is divided into a lower platform portion 114A and an upper platform portion 114B. The lower platform portion 114A will be of essentially conventional construction similar to the platform 14 of FIG. 1. The upper platform portion 114B is positioned above the lower platform portion 114A but is secured thereto by the support 114C.

Also included in this second embodiment of the invention is a fixed platform 118 supported by the leg 120.

The method of using the embodiment of the invention shown in FIG. 3 is essentially the same as discussed above with respect to FIG. 1. That is, the magnet 16 is positioned on the lower platform portion 114A at the left side thereof as shown and the force transducer 112 is zeroed out to remove the gravitational force of the magnet. The sample 22 is then placed on the platform 118 directly above the magnet 16. The magnetic force between the sample 22 and the magnet 16 is then noted on the force transducer 112. In order to determine the gravitational force of the sample 22, all that is required is to move the sample from the support platform 118 to the upper platform portion 114B as shown in FIG. 3.

As should be recognized by those skilled in the art, the above-described method will function properly with substantially any size sample 22 with an area no larger than that of the magnet. However, because the magnetic field of the magnet 16 weakens with the perpendicular distance from the magnet, quantitative results can be obtained after an adjustment to the F/G value is made based on the sample thickness and a specific calibration curve is obtained with prepared standards of known thicknesses and known percent contents of the component of interest, i.e. an element (e.g. iron, nickel, cobalt), compound, mineral, metal, alloy etc. with the property of magnetic susceptibility or permanent magnetism.

The invention has many uses in addition to screening for the presence of asbestos. For example, one may wish to determine, for expedient quality control or related purposes, the presence and possible quantity of iron in various enriched food products such as flour and cereal, certain vitamins and pharmaceuticals, inks etc. In essence, the invention can be used to determine the presence and/or concentration of substantially any component of a material that exhibits magnetic susceptibility or permanent magnetism.

The present invention may not necessarily establish the presence or concentration of a specific magnetically susceptible component in a sample of a material since even a positive result may be caused by the presence of a different magnetically susceptible or magnetic component other than the one suspected. The method can be used, however, to screen samples. That is, when the method of the present invention is used in connection with a particular sample, if it is found that it exhibits no magnetic susceptibility or permanent magnetism, there is no reason to test the same further. If, however, it is determined that there is a component of the sample possessing the property of magnetic susceptibility or permanent magnetism, the sample can then further be tested utilizing microscopic, chemical, spectroscopic or radioactive methods, involving electrons, electromagnetic radiation, neutrons, etc. as primary excitation sources. Thus, the method of the present invention can be used for screening larger numbers of samples in order to minimize those that must be subjected to more extensive analysis.

As an example of another manner of use, it can also be easily and readily used to compare the relative concentration of magnetically susceptible or magnetic components in samples of equally intended substance, mass and size such as medicinal or vitamin pills. Quantitative analysis is also possible by means of thickness adjustments and specific calibrations.

The present invention may be embodied in other specific forms without departing from the spirit or essential attributed thereof and accordingly, reference should be made to the appended claims rather than to the foregoing specification as indicating the scope of the invention.

I claim:

1. A method of determining the presence of a magnetically susceptible substance in a sample of a material being tested comprising the steps of:
    obtaining a sample of said material;
    providing a platform;
    providing a magnet;
    arranging said platform and said magnet in substantial vertical alignment but vertically spaced from each other by a predetermined distance;
    placing said sample on said platform so as to be vertically aligned with said magnet, and
    utilizing a force transducer, measuring the magnetic force exerted on said sample by said magnet in the vertical direction by measuring the gravitational force on one of said magnet or sample outside of the presence of the other, measuring the gravitational force on one of said magnet or sample in the presence of the other and comparing the two gravitational force measurements.

2. The method as claimed in claim 1 further including the step of determining the gravitational force of said sample out of the presence of said magnet and dividing the measured magnetic force by the gravitational force to obtain the magnetic force per unit sample gravitational force.

3. The method as claimed in claim 2 further including the step of making an adjustment for sample thickness.

4. The method as claimed in claim 1 wherein said substance is magnetically susceptible or contains a permanently magnetic component.

* * * * *